（12） United States Patent
Wei et al.

(10) Patent No.: US 7,396,653 B2
(45) Date of Patent: *Jul. 8, 2008

(54) CELL MIGRATION ASSAY

(75) Inventors: Zheng Wei, Redwood City, CA (US);
Zhenhua Miao, San Jose, CA (US)

(73) Assignee: ChemoCentryx, Inc., Mt. View, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 11/788,334

(22) Filed: Apr. 17, 2007

(65) Prior Publication Data

US 2007/0196855 A1     Aug. 23, 2007

Related U.S. Application Data

(63) Continuation of application No. 10/154,399, filed on May 22, 2002, now Pat. No. 7,282,338.

(60) Provisional application No. 60/296,682, filed on Jun. 7, 2001.

(51) Int. Cl.
*G01N 33/566* (2006.01)
*G01N 33/567* (2006.01)
*C12M 1/00* (2006.01)

(52) U.S. Cl. .................. 435/7.1; 435/7.2; 435/7.21; 435/7.8; 530/350; 530/399

(58) Field of Classification Search ............... None
See application file for complete search history.

(56) References Cited

U.S. PATENT DOCUMENTS

| 4,816,567 | A | 3/1989 | Cabilly et al. |
|---|---|---|---|
| 6,448,054 | B1 | 9/2002 | Poznansky et al. |
| 6,451,522 | B2 | 9/2002 | LaRosa |
| 6,689,570 | B2 | 2/2004 | Andrew |
| 6,884,574 | B2 | 4/2005 | Andrew |
| 7,282,338 | B2 * | 10/2007 | Wei et al. ............... 435/7.1 |

FOREIGN PATENT DOCUMENTS

| WO | WO 97/31949 | 9/1997 |
|---|---|---|
| WO | WO 98/09171 | 3/1998 |

OTHER PUBLICATIONS

Ali et al. Chemoattractant Receptor Cross-desensitization. The Journal of Biological Chemistry, vol. 274, No. 10, pp. 6027-6030 (1999).*
2003/0166143 A1.
Ancelin et al., "Vascular Endothelial Growth Factor VEGF189 Induces Human Neutrophil Chemotaxis In Extravascular Tissue Via An Autocrine Amplification Mechanism," *Laboratory Investigation*, 84:502-512 (Feb. 16, 2004).
Ausubel, F.M., R. Brent, R.E. Kingston, D.D. Moore, et al., "Current Protocols in molecular biology," *John Wiley & Sons*, New York (1987).

Bacon, K.B. et al., "Contrasting in vitro lymphocyte chemotactic activity of the hydroxyl enantiomers of 12-hydroxy-5, 8, 10, 14-eicosatetraenoic acid," *Br. J. Pharmacol.*, 95:966-974 (1988).
Baggiolini et al., *Annu. Rev. Immunol*, 15:675-705 (1997).
Baggiolini et al., *Advances in Immunology*, 55;97-179 (1994).
Behar et al., "Neurotrophins Stimulate Chemotaxis of Embryonic Cortical Neurons," *European Journal of Neuroscience*, 9:2561-2570 (Jun. 18, 1997).
Deng, et al., *Nature*, 381:661-666 (1996).
Ellington, A.D., et al., "In vitro Selection of RNA Molecules that Bind Specific Ligands," *Nature*, 346:818-822 (1990).
Ernst et al., An Annexin 1 N-Terminal Peptide Activates Leukocytes by Triggering Different Members of the Formal Peptide Receptor Family, *Journal of Immunology*, 172:7669-7676 (Apr.6, 2004).
Nakamura et al., "Signals Via FGF Receptor 2 Regulate Migration of Endothelial Cells," *Biochemical and Biophysical Research Communications*, 289:801-806 (Nov. 9, 2001).
Penfold, M. E. et al., "Cytomegalovirus Encodes a Potent Alpha Chemokine," *Proc. Natl. Acad. Sci. USA*, 96:9839-9844 (1999).
Polk et al., "Epidermal and Hepatocyte Growth Factors Stimulate Chemotaxis in an Intestinal Epithelial Cell Line," *Am J. Physiol.*, 277:C1149-CI159 (1999).
Postma et al., "Chemotaxis Inhibitory Protein of *Staphylococcus aureus* Binds Specifically to the C5a and Formylated Peptide Receptor," *Journal of Immunology*, 172:6994-7001 (Mar. 18, 2004).
Rosenfeldt et al., "The Sphingosine-I-Phosphate Receptor EDG-I is Essential for Platelet-Derived Growth Factor-Induced Cell Motility," *Biochemical Society Transactions*, 29(6):836-839 (Jun. 30, 2001).
Riechmann, L., M. Clark, H. Waldmann, G. Winter, "Reshaping Human Antibodies for Therapy," *Nature*. 332-323-7 (1988).
Rossi, D., and A. Zlotnik, "The Biology of Chemokines and their Receptors," *Annu. Rev. Immunol.*, 18:217-242 (2000).
Schratzberger et al., "Differential Chemotactic Activities of Sensory Neurpeptides for Human Peripheral Blood Mononuclear Cells" *Journal of Immunology*, 158:3895-3901 (Jan. 13, 1997).
Serhan et al., "Cutting Edge: Nociceptin Stimulates Neutrophil Chemotaxis and Recruitment. Inhibition byAspirin-Triggered-15-Epi-Lipoxin A4," *Journal of Immnology*, 166:3650-3654 (Jan. 19, 2001).
Shizukuda et al., "Vascular Endothelial Growth Factor-Induced Endothelial Cell Migration and Proliferation Depend on a Nitric Oxide-Mediated Decrease in Proteine Kinase Co Activity," *Circ. Res.*, 85:247-256 (Aug. 6, 1999).
Song et al., "CB1 Cannabinoid Receptor-Mediated Cell Migration," *Journal of Pharmacology and Experimental Therapeutics*, 294(1):204-209 (Mar. 22, 2000).
Tager et al., "Leukotriene B4 Receptor BLT1 Mediates Early Effector T Cell Recruitment," *Nature Immunology*, 10(4):982-990 (Oct. 2003).
Tuerk, C. et al., "Systemic Evolution of Ligands by Exponential Enrichment: RNA Ligands to Bacteriophage T4 DNA Polymerase," *Science*, 249:505-510 (1990).

(Continued)

*Primary Examiner*—Marianne P Allen
*Assistant Examiner*—Regina M DeBerry
(74) *Attorney, Agent, or Firm*—Brinks Hofer Gilson & Lione (57) ABSTRACT

The present invention is directed to a modified cell migration assay allowing for improved identification and discrimination of chemokine receptor antagonists from non-specific blockers.

22 Claims, 7 Drawing Sheets

OTHER PUBLICATIONS

Verhoeyen, M., C. Milstein, and G. Winter, "Reshaping Human Antibodies: Grafting an Antilysozyme Activity." *Science*, 239:1534-6 (1988).

Yule et al., "Migration of 3T3 and Lung Fibroblasts in Response to Calcitonin Gene-Related Peptide and Bombesin," *Experimental Lung Research*, 25:261-273 (Aug. 5, 1998).

Zhang et al., "VEGF is a Chemoattractant for FGF-2-Stimulated Neural Progenitors," *Journal of Cell Biology*, 163(6): 1375-1384 (Dec. 22, 2003).

Fiedler et al., "To Go or Not to Go: Migration of Human Mesenchymal Progenitor Cells Stimulated by Isoforms of PDGF," *Journal of Cellular Biochemistry*, 93:990-998 (May 26, 2004).

Forster, R., et al., "CCR7 Coordinates the Primary Immune Response by Establishing Functional Microenvironments in Secondary Lymphoid Organs", *Cell*, 99; 23-33 (1999).

Gutzmer et al., "Human Monocyte-Derived Bendritic Cells Are Chemoattracted to C3a After Up-Regulation of the C3a Receptor with Interferons," *Immunology*, 111:435-443 (Jan. 9, 2004).

Haynes et al., "Inhibition of C5a-Induced Neutrophil Chemotaxis and Macrophage Cytokine Production in Vitro by a New C5a Receptor Antagonist," *Biochemical Pharmacology*, 60:729-733 (Mar. 13, 2000).

Hesselgesser et al., *J Biol Chem*, 273(25):15687-92 (1998).

Horuk, *Trends Pharm. Sci.*, 15:159-165 (1994).

Idzko et al., "Nucleotides Induce Chemotaxis and Actin Polymerization in Immature But Not Mature Human Dendritic Cells Via Activation of Pertussis Toxin-Sensitive Pty Receptors," *Immunobiolo*, 100(3):925-932 (Mar. 13, 2002).

Jayasena, S.D., "Aptamers: An Emerging Class of Molecules that Rival Antibodies in Diagnostics," *Clin Chem*. 45:1628-50 (1999).

Jones, P.T., P.H. Dear, J. Foote, M.S. Neuberger, et al., "Replacing the Complementarity-determining Regions in a Human Antibody with Those from a Mouse," *Nature*, 321:522-5 (1986).

Kledal, T.N. et al, "A Broad-spectrum Chemokine Antagonist Encoded by Kaposi's Sarcoma-associated Herpesvirus," *Science*, 277:1656-1659 (1997).

Klein et al., "Identification of Surrogate Agonists for the Human FPLR-1 Receptor by Autocrine Selection in Yeast," *Nature Biotechnology*, 16:1334-7 (1998).

Lamb et al., "EGF Mediates Monocyte Chemotaxis and Macrophage Proliferation and EGF Receptor is Expressed in Atherosclerotic Plaques," *Atherosclerosis*, 176:21-26 (Apr. 20, 2004).

Ling et al., "Histamine H4 Receptor Mediates Eosinophil Chemotaxis with Cell Shape Change and Adhesion Molecule Upregulation," *British Journal of Pharmacology*, 142:161-171 (Feb. 9, 2004).

Loetscher et al., "The Ligands of CXC Chemokine Receptor 3, I-TAC, Mig, and IP10, Are Natural Antagonists for CCR3", *J. Biol. Chem.*, 276(5):2986:91 (2001).

Migeotte et al., "Identification and Characterization of an Endogenous Chemotactic Liquid Specific for FPRL2," *Journal of Experimental Medicine*, 201(1):83-93 (Jan. 3, 2005).

Mimura et al., "Inhibitory Effect of the 4 Aminotetrahydroquinoline Derivatives, Selective CRTH2 Antagonists, on Eosinophil Migration Induced by Prostaglandin D2," *Journal of Pharmacology and Experimental Therapeutics*, as DOI:10.1124 et. 104.081539 (Mar. 29, 2005).

* cited by examiner

CELL MIGRATION ASSAY

RELATED APPLICATIONS

This application is a continuation application of U.S. application Ser. No. 10/154,399. filed May 22, 2002, now U.S. Pat. No. 7,282,338 which claims priority to U.S. provisional application Ser. No. 60/296,682 filed Jun. 7, 2001, which is incorporated herein by reference in its entirety.

FIELD OF THE INVENTION

The present invention is directed to an assay for identifying antagonists of chemoattractant receptors, such as chemokine receptors. One advantage of the assay compared with prior assays is its ability to discriminate valid chemoattractant receptor antagonists from those compounds that generate false positive and negative signals.

BACKGROUND

High-throughput screening (HTS) methods for identifying antagonists of chemoattractant receptors often rely on detecting perturbations in downstream events, such as cell migration. In the case of chemokine receptors, leukocyte cell migration is often assayed. However, compounds disrupting cell membranes or blocking downstream events mimic these outcomes, masquerading as candidate antagonists. Considerable effort is then required to distinguish the genuine antagonists from those compounds or molecules that caused false positive signals. Identifying true antagonists, which represent only a very small fraction of the large collections of candidate antagonists analyzed in high-throughput screens, is a formidable task. Realizing any savings in time or expense can bring a new drug to patients more quickly and less expensively.

Conventional assays that are adapted for use in HTS methods for screening small molecule antagonists of ligand-receptor interactions and signaling are usually one-dimensional. That is, they isolate and assay only the ligand-receptor interaction or the cellular signaling that ligand binding initiates, but not both. Because of this separation of physical interaction (ligand-receptor binding) from function (receptor signaling and downstream events), false positive signals are often observed, slowing discovery and development. False positives are molecules that give the desired result for undesirable reasons; they are often seen in screens for small molecule antagonists. Small molecules that initially appear to be inhibitors of receptor-ligand binding interactions (a desired result) may give such a result, for example, either by inhibiting the receptor-ligand interaction by binding the target receptor or ligand (desirable reasons), or by sickening or killing cells, or wielding other undefined effects (undesirable reasons).

Furthermore, conventional drug discovery formats for chemoattractant receptor antagonists fail to identify all clinically important molecules, a consequence of false negative signals. False negatives mean that clinically important molecules are undetected and remain undiscovered. For example, a molecule that permits chemoattractant receptor ligand-chemoattractant receptor binding, but inhibits chemoattractant receptor signaling, will be hidden in an initial screen for inhibitors of ligand binding.

Chemoattractant molecules attract cells. For example, chemokines, a group of more than 40 small peptides (generally 7-10 kDa in size), act as molecular beacons for the recruitment, activation, and directed migration of T lymphocytes, neutrophils and macrophages of the immune system, flagging pathogens and tumor masses for destruction. While defending the individual from invading pathogens and tumors, the immune system can cause disease when improperly regulated. Chemokine-receptor binding is linked to G-protein-coupled signaling cascades to mediate chemoattractant and chemostimulant signaling functions.

Inappropriate chemokine signaling can either promote infections when not properly triggered (Forster et al., 1999) or lead to diseases associated with defective chemokine signaling, including asthma, allergic diseases, multiple sclerosis, rheumatoid arthritis, and atherosclerosis (reviewed in Rossi and Zlotnick, 2000). Because chemokines play pivotal roles in inflammation and lymphocyte development, the ability to specifically manipulate their activity will have enormous impact on ameliorating and halting diseases that currently have no satisfactory treatment. Chemokine receptor antagonists can be used to obviate the generalized and complicating effects of costly immunosuppressive pharmaceuticals in transplant rejection (reviewed in DeVries et al., 1999).

To expedite the identification of chemoattractant receptor antagonists, such as those for chemokine receptors, an assay that weeds out false signals by testing both chemoattractant receptor binding and a biological function would hasten drug development.

SUMMARY OF THE INVENTION

In a first aspect, the invention provides methods for identifying a chemoattractant receptor antagonist. A cell having a chemoattractant receptor is incubated with a candidate antagonist in the presence of an excess of optimal ligand concentration for the chemoattractant receptor, and then cell migration is assayed. Cell migration indicates that the candidate antagonist is an antagonist.

In one aspect, the invention provides methods for identifying a chemokine receptor antagonist. A cell expressing a chemokine receptor is incubated with a candidate antagonist in the presence of an inhibitory concentration of chemokine ligand, and then cell migration is assayed. Cell migration indicates that the candidate antagonist is an antagonist.

The invention also provides for kits containing a solution with an inhibitory concentration for migration of chemokine for a chemokine receptor bearing cell. In addition, such kits may also include a cell migration apparatus.

In another aspect, the invention provides methods for identifying a chemokine receptor antagonist. A candidate antagonist of a chemokine receptor is first identified in a conventional assay. In a subsequent step, the candidate antagonist is incubated with a chemokine receptor bearing cell in the presence of inhibitory concentration of ligand, and then cell migration is assayed. Cell migration confirms that the candidate antagonist is an antagonist.

These and other embodiments are discussed in detail below.

DETAILED DESCRIPTION OF THE INVENTION

The reversed-activation of migration (RAM) assay of the invention identifies and discriminates antagonists while significantly decreasing the prevalence of confounding false positive and negative signals found in other assays. The time and labor involved to confirm a potential pharmaceutical compound is therefore greatly reduced.

The methods of the invention include:

(1) incubating a cell comprising a chemoattractant receptor, such as a chemokine receptor, with a candidate antagonist;

(2) contacting the cell with an inhibitory concentration of a ligand for the chemoattractant receptor; and (3) assaying cell migration.

Cell migration is used to identify the candidate antagonist as an antagonist.

The method may further comprise a "pre-step" in which the concentration of a chemoattractant ligand (such as a chemokine) that inhibits cell migration is determined, the "inhibitory concentration" of a ligand for a chemoattractant receptor. Additional steps may be added, depending on the type of cell or agent being used, the assay, etc.

Figure 1:
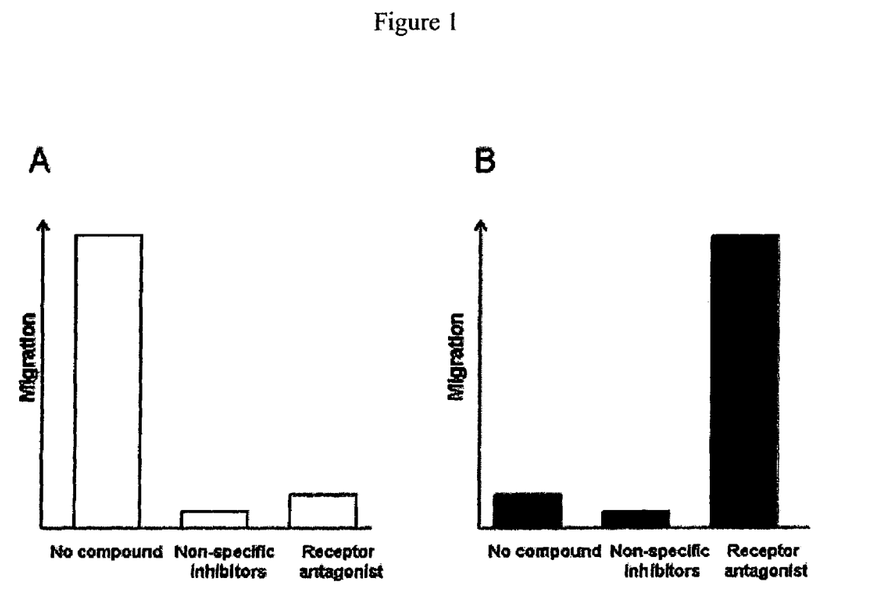
FIG. 1. shows graphs depicting the selective activation of cell migration by chemokine receptor antagonist by the (B) "reversed-activation of migration" (RAM) assay compared to (A) conventional assays.

While conventional screens for antagonists of cell migration measure the reduction of cell migration—a reduction in activity—RAM assays measure the activation of cell migration, an increase in activity (FIG. 1A, conventional migration assay; FIG. 1B, RAM assay). In the RAM assay, cells are challenged to migrate in the presence of migration-inhibitory concentrations of chemoattractants in response to a candidate antagonist; in a conventional assay, cells are challenged to migrate in response to a chemoattractant in the presence of a candidate antagonist. A compound that gives a false positive signal in a conventional cell migration assay (inhibiting migration) will fail to activate cell migration in the RAM format. In the RAM assay, only a true antagonist activates migration. This distinction allows for simple identification of authentic antagonists.

Another advantage of the RAM assay is that the identified antagonists are more likely to be therapeutically useful than those identified in conventional assays. A therapeutic chemoattractant receptor antagonist is specific for that receptor, exerting its effect through the receptor. Such an antagonist reduces the effective affinity between the chemoattractant and the receptor without compromising the physical integrity of the cell or completely disrupting the downstream signaling events leading to migration. A false positive identified in a conventional assay lacks at least one of these characteristics.

Figure 2:
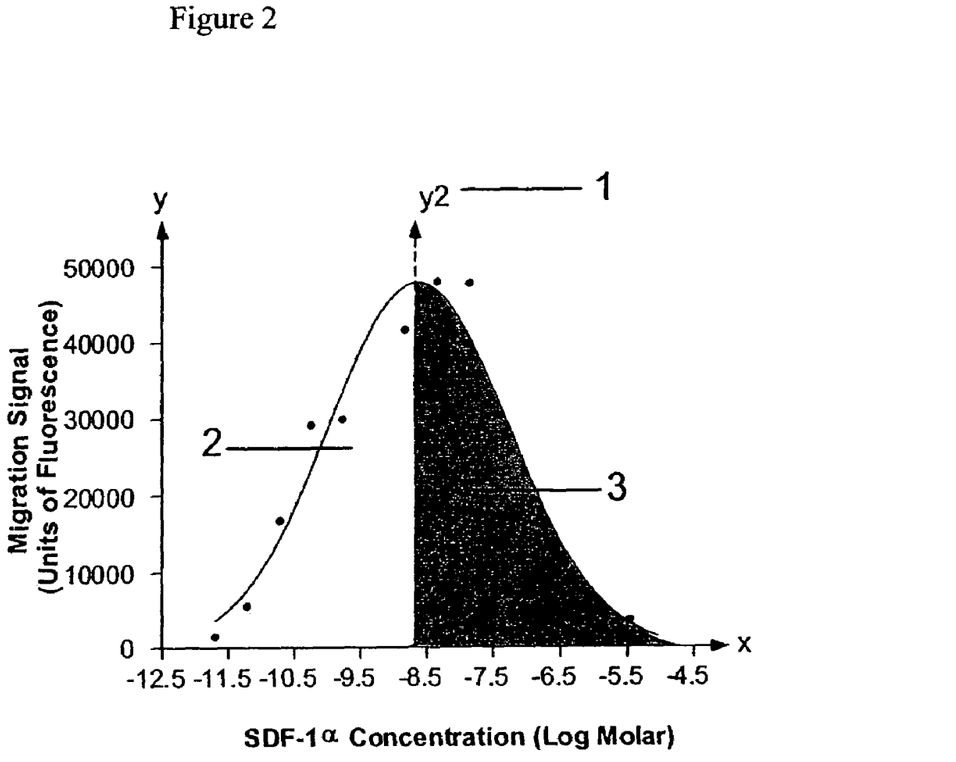
FIG. 2. shows a graph depicting the dose response curve for CXCR4 chemokine receptor-SDF ligand interaction, relating to cell migration. X-axis, chemokine concentration (expressed as log); Y-axis, cell migration as measured in a cell migration assay (expressed as units of fluorescence).
Figure 3:
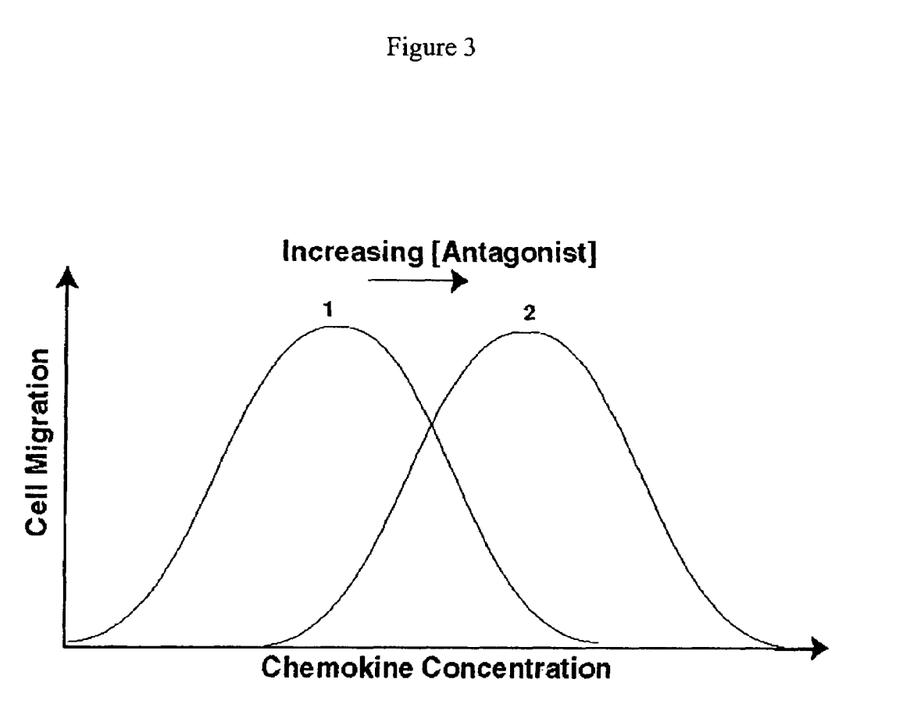
FIG. 3 shows a graph depicting representative curves that demonstrate the right-shift of the migration curve in the presence of an antagonist under RAM conditions. X-axis, chemokine concentration (expressed as log); Y-axis, cell migration as measured in a cell migration assay (numbers of cells).

One possible explanation for the success of the RAM assay is based on the observation that for a cell to migrate, the cell must have front end-back end polarity. Such polarity is often initiated by extracellular signals, such as chemokines. For cell migration, this polarity is achieved by a differential degree of chemoattractant receptor occupancy at the two ends of the cell. However, high concentrations of chemoattractant inhibit migration because all receptors are occupied in all directions of the cell; the cell lacks a directional cue. If increasing concentrations of ligand are plotted in relation to cell migration, a bell-shape curve is observed (an example is shown in FIG. 2). A receptor antagonist that reduces the effective affinity of a chemoattractant for a receptor allows the ligand to behave like a ligand with lower affinity. The bell-shape curve, first observed in the absence of antagonists, shifts to the right in the presence of increasing concentrations of antagonist (see e.g., FIG. 3). This is one possible explanation for the success of the present invention. The inventors do not intend to be limited by this proposal.

Definitions

A "cell migration assay" tests the capacity of a cell to migrate in response to a signal.

An "inhibitory concentration" of a chemoattractant is one that inhibits cell migration. This concentration is greater than one that activates cell migration.

A "chemoattractant receptor" is a receptor that binds a chemoattractant ligand, inducing cell migration. For example, a chemokine receptor is a chemoattractant receptor whose (chemoattractant ligand is at least one chemokine.

In the following sections, the RAM assay is illustrated using chemokines and chemokine receptors. However, any chemoattractant and chemoattractant receptor that induces cell migration may be used. Table A shows some examples of known chemoattractant receptors and some of their ligands.

TABLE A

Exemplary human chemoattractant receptors and exemplary ligands[1]

| Receptor | Examples of ligands[2] |
|---|---|
| BLT1 | Leukotriene B4 |
| PDGFR | Platelet-Derived Growth Factor |
| FPR | fMLP |
| FPRL1 | Unknown |
| FMLP receptor-like receptor | Unknown |
| CRTH2 | prostaglandin D2 |
| C3aR | C3a |
| C5aR | C5a |
| Noci-R | Nociceptin |
| EDG family | Sphingosine 1-phosphate |
| CB1 | Cannabinoids |
| VEGFR | Vascular endothelial growth factor |
| EGFR | Epidermal growth factor |
| FGFR | Fibroblast growth factor |
| P2Y receptor | P2Y |
| CTR | Calcitonin |
| CRLR | Calcitonin gene-related peptide (CGRP) |
| Histamine receptor | Histamine |
| Thrombin receptor | Thrombin |
| TrkB | Brain-derived neurotrophic factor (BDNF) |

[1] This list of chemoattractant receptors is not meant to be exhaustive.
[2] Only examples of some ligands for each receptor are given. This list is not meant to be exhaustive.

RAM Assay

In the RAM assay, a chemokine-bearing cell is incubated with a candidate antagonist and then contacted with an inhibitory concentration of a ligand for the target chemokine receptor. The ability of the cell to migrate is then assayed. If the cell migrates in the presence of a candidate antagonist in the RAM assay, then a positive signal has been observed. "Antagonist" includes any molecule that partially or fully blocks, inhibits, or neutralizes a biological activity, such as cell migration. Similarly, "agonist" includes any molecule that mimics a biological activity of molecule, such as a chemokine. Molecules that can act as agonists or antagonists include small organic molecules, macromolecules, antibodies or antibody fragments, fragments or variants of chemokines, peptides, etc. A "candidate antagonist" is a compound that is being tested for antagonist activity; likewise, a "candidate agonist" is a compound that is being tested for agonist activity.

Any cell migration assay format may be used, such as the ChemoTx® system (NeuroProbe, Rockville, Md.) or any other suitable device or system (Bacon et al., 1988; Penfold et al., 1999). In brief, these cell migration assays work as follows. After harvesting and preparing the cells bearing the active target chemokine receptor, the cells are mixed with candidate antagonists. The mixture is placed into the upper chamber of the cell migration apparatus. To the lower chamber, an inhibitory concentration of chemokine ligand is added. The migration assay is then executed, terminated, and cell migration assessed.

Figure 4:
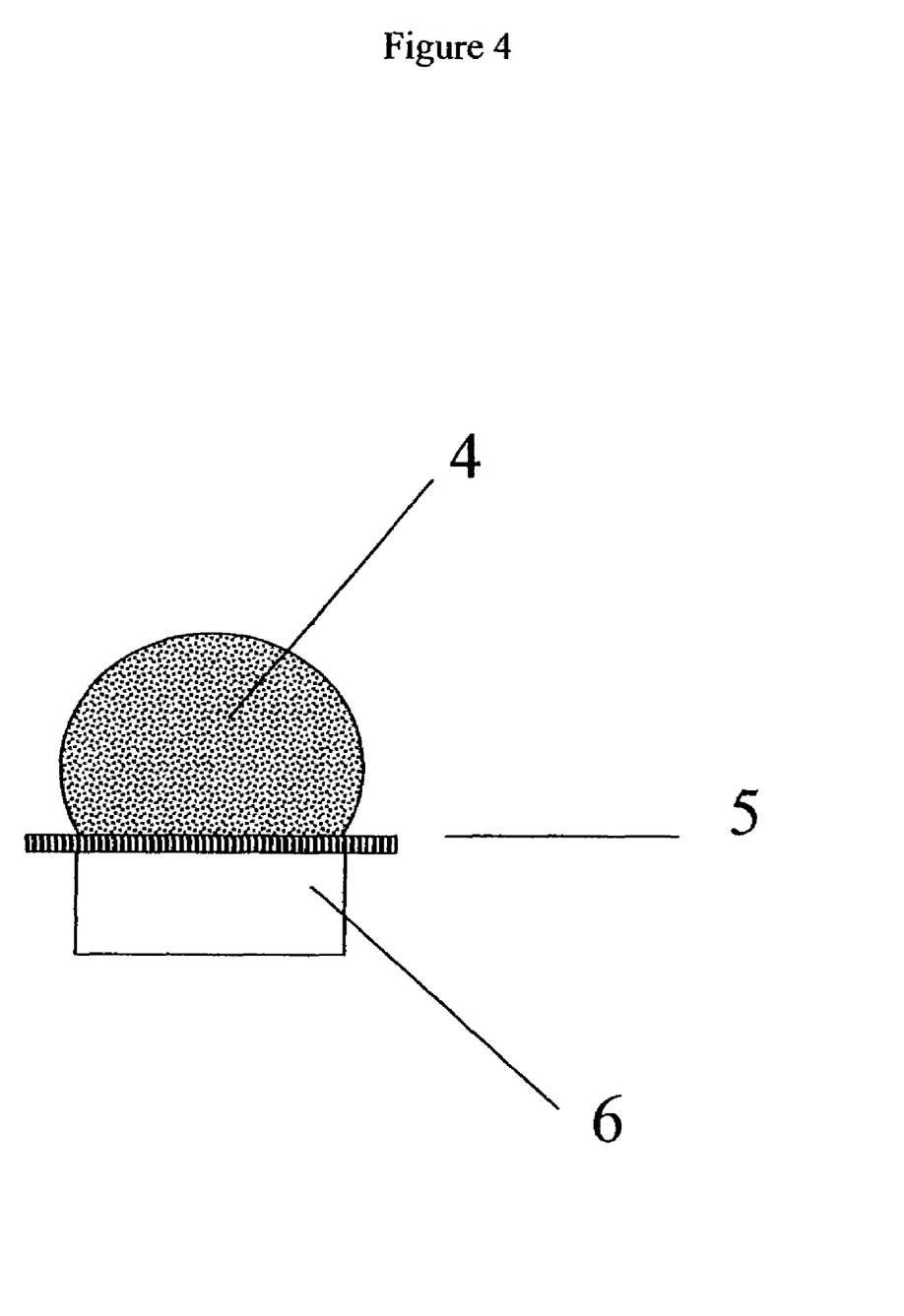
FIG. 4. depicts a schematic of a conventional cell migration assay.

To start the RAM assay, the solution of the inhibitory concentration of chemokine ligand is added to the lower chamber (6, FIG. 4) of a cell migration apparatus, and the cell suspension is placed into the upper chamber (4, FIG. 4) that is separated by a porous membrane (5, FIG. 4). The cells are incubated under culture conditions (37° C. for human cells) for 60 to 180 minutes in a humidified tissue culture incubator. The incubation period depends on the cell type and if necessary, can be determined empirically.

At the end of the incubation period, the assay is terminated. For example, non-migrating cells on the upper chamber of the apparatus are removed, using a rubber scraper or other manual method; enzymatically or chemically, e.g., EDTA and EGTA solutions. The membrane (5, FIG. 4) that separates the two chambers is then removed from the apparatus and rinsed with Dulbecco's phosphate buffered saline (DPBS) or water. The number of cells that migrate into the lower chamber is then determined.

The concentration of candidate antagonist to be screened in RAM assays may range from sub-nanomolar to millimolar. Screening a collection of small molecule compounds (such as a library synthesized by combinatorial chemistry), the concentration of candidate antagonists is typically about 1-20 μM. "Compound" includes small inorganic and organic molecules, macromolecules, peptides, proteins, polypeptides, nucleic acids, and antibodies.

Determining Inhibitory Concentrations of Ligand

A dose response of cell migration to a chemokine ligand can be performed to define the inhibitory concentrations of a chemokine ligand. Any standard method for determining dose response curves can be used. One such method includes harvesting cells expressing the target chemokine receptor, adding the cells to a cell migration device in the presence of increasing amounts of chemokine, measuring cell migration, plotting cell migration versus chemokine concentration, and then calculating from the graph those chemokine concentrations that inhibit cell migration.

As an example, a conventional cell migration assay, such as the ChemoTx® system (NeuroProbe, Rockville, Md.) or any other suitable device or system (Bacon et al., 1988; Penfold et al., 1999) may be used. To obtain a dose response curve, cells expressing the target receptor are gathered. A chemokine ligand is prepared in a concentration series by serial dilution in a buffer. The concentration range is typically between 0.1 nM and 10 mM, but will vary with ligand.

To start the cell migration assay, solutions of the various chemokine ligand concentrations are added to the lower chamber (6, FIG. 4) of a cell migration apparatus, and the cell suspension is placed into the upper chamber (4, FIG. 4) that is separated by a porous membrane (5, FIG. 4). The cells are incubated under culture conditions (37° C. for human cells) for 60 to 180 minutes in a humidified tissue culture incubator. The incubation period depends on the cell type and if necessary, can be determined empirically.

After terminating cell migration, non-migrating cells on the upper chamber of the apparatus are removed, using a rubber scraper or other manual method; enzymatically or chemically, e.g., EDTA and EGTA solutions. The membrane (5, FIG. 4) that separates the two chambers is then removed from the apparatus and rinsed with Dulbecco's phosphate buffered saline (DPBS) or water. The number of cells that migrate into the lower chamber is then determined.

Cell migration (Y-axis) is then plotted against the log (chemokine concentration) (X-axis); a bell-shaped curve is observed (FIG. 2; see Examples). From this plot (FIG. 2), the lowest concentration of chemokine that inhibits cell migration can be determined. For ease of reference, a second Y-axis ($y_2$, 1, FIG. 2) can be drawn through the bell curve, intersecting at its apex (maximal cell migration) and the corresponding value on the X-axis. Those concentrations to the left of the $Y_2$-axis (lower) are stimulatory (2, FIG. 2); those to the right (higher) are inhibitory (3, shaded region, FIG. 2). These concentrations are the "inhibitory concentrations" for cell migration (chemotaxis). For example, to determine the concentration at with migration is inhibited by 90% of the maximum (to the right of the $Y_2$-axis, the "inhibitory" concentrations), the value corresponding to 10% of maximal cell migration on the Y-axis is located. If the maximal cell migration signal is, e.g., $3.5 \times 10^4$ cells, 10% thereof would be 350 ($3.5 \times 10^4 \times 0.1$). The inhibitory ligand concentration is then determined by locating the corresponding X-axis coordinate. Preferably, the level of inhibition is 50%, 60%, 70% or 80% of maximal cell migration. More preferably, the level of inhibition is 90% or even more preferably 95% or 100% inhibition as compared to the maximal signal for migration. The determined chemokine concentration varies and depends on the nature of the receptor, the chemokine ligand and the target cell. Varying the degree of chemotactic inhibition can be used to modulate the sensitivity of the RAM assay.

Application of RAM Assays in Comprehensive Screens for Therapeutic Antagonists

RAM assays can be performed in conjunction with any other assay used to screen for chemokine receptor antagonists. Not only is the RAM format useful as a primary HTS step, but it also provides a confirmatory or secondary assay for candidate antagonists identified in other assays. For example, a HTS method that measures $Ca^{2+}$ mobilization, including those based on the FLIPR™ system (Molecular Devices Corp., Sunnyvale, Calif.) or other reporter-based methods which assay increases in free intracellular $Ca^{2+}$ levels, can be used as a primary assay. RAM assays can be used to confirm such candidates, or vice-versa. As a secondary assay, RAM would discriminate those candidate antagonists that exert non-specific effects. When RAM assays are used with other HTS methods, a means for discriminating true hits from non-specific blockers is provided.

The RAM assay can be applied to any other assay format measuring cell migration or receptor activation, including methods that do not require migration of cells across a porous membrane. More useful technologies offering higher throughput and lower cost may be developed based on use of the RAM concept.

Cells for use in the RAM Assay

Cells expressing a target chemokine receptor (or chemoattractant receptor) for use in the RAM assay may be gathered by a variety of methods, for example by centrifugation after collection from a subject or release from culture, and then resuspended in a buffer at an appropriate density, depending on cell type and cell size. Convenient cell concentrations range from about $1 \times 10^6$ to $1 \times 10^7$ cells/ml; often about $2.5 \times 10^6$ cells/ml is suitable.

Chemokine Receptors and Ligands

Cells that can be assayed in the RAM format include all those that express at least one chemokine receptor on the cell surface, such as human monocytes, or other cells engineered to express recombinant chemokine receptors and are competent to activate cell migration. Known chemokine receptors and some of their ligands are shown in Table B. Examples of chemokine receptors include, but are not limited to, the CXC class, e.g., CXCR1, CXCR2, CXCR3, CXCR4, CXCR5; the CC class, CCR1, CCR2, CCR3, CCR4, CCR5, CCR6, CCR7, CCR8, CCR9, CCR10 and CCR11; the CX3CR class, such as CX3CR1 and the XCR class, such as XCR1.

An example of a non-chemokine chemoattractant receptor is formyl peptide receptor like protein 1 (FPRL1); the ligands for which are w-peptide1 and w-peptide2 (Klein et al., 1998). Also see Table A for other examples.

TABLE B

Summary of the known chemokine receptors and some of their known human ligands (Rossi and Zlotnik, 2000)

| Receptor | Human ligands |
| --- | --- |
| CXCR1 | IL-8, GCP-2 |
| CXCR2 | IL-8, GCP-2, Gro α, Gro β, Gro γ, ENA-78, PBP |
| CXCR3 | MIG, IP-10, I-TAC |
| CXCR4 | SDF-1/PBSF |
| CXCR5 | BLC/BCA-1 |
| CCR1 | MIP-1α, MIP-1β, RANTES, HCC-1, 2, 3, and 4 |
| CCR2 | MCP-1, MCP-2, MCP-3, MCP-4 |
| CCR3 | eotaxin-1, eotaxin-2, MCP-3 |
| CCR4 | TARC, MDC, MIP-1α, RANTES |
| CCR5 | MIP-1α, MIP-1β, RANTES |
| CCR6 | MIP-3α/LARC |
| CCR7 | MIP-3β/ELC, 6Ckine/LC |
| CCR8 | I-309 |
| CCR9 | TECK |
| XCR1 | Lymphotactin |
| CX3CR1 | Fractalkine/neurotactin |
| CXCR6 | CXCL16 |
| CCR10 | CTACK |

Chemokines that can be used in the RAM assay include all known chemokines. Examples of chemokines include, but are not limited to, IL-8, GCP-2, Gro α, Gro β, Gro γ, ENA-78, PBP, MIG, IP-10, I-TAC, SDF-1 (PBSF), BLC (BCA-1), MIP-1α, MIP-1β, RANTES, HCC-1, -2, -3, and -4, MCP-1, -2, -3, and -4, eotaxin-1, eotaxin-2, TARC, MDC, MIP-3α (LARC), MIP-3β (ELC), 6Ckine (LC), I-309, TECK, lymphotactin, fractalkine (neurotactin), TCA-4, Exodus-2, Exodus-3 and CKβ-11.

Chemokine receptor/ligand combinations include those associated with inflammatory disorders, infectious diseases and transplant rejection. Such combinations include CX3CR1/fractalkine (transplantation), CCR5/MIP-1α, MIP-1β, or RANTES (HIV), CXCR4/SDF-1 (HIV); and CCR7/MIP-3β, ELC or 6Ckine LC (inflammatory or allergic diseases, e.g. asthma, multiple sclerosis, etc.).

Candidate Antagonists

Any molecule or compound can be screened for chemokine receptor antagonist activity. Compounds that inhibit chemokine receptor/ligand activities, such as activating cell migration or modulating intracellular $Ca^{2+}$ concentrations are candidate antagonists.

Such molecules that may exert such antagonistic effects include small molecules that bind to chemokine receptors or their ligands. Examples of small molecule antagonists include small peptides, peptide-like molecules, preferably soluble and synthetic non-peptidyl organic or inorganic compounds. Other potential antagonist molecules include nucleic acids such as aptamers and antibodies. These molecules may be collected into various libraries can be quickly screened for novel chemokine receptor antagonists using the RAM assay.

Almost any antibody (Ab) that inhibits chemotactic cell migration is also a candidate antagonist. Examples of antibody antagonists include polyclonal, monoclonal, single-chain, anti-idiotypic, chimeric Abs, or humanized versions of such Abs or fragments. Abs may be from any species in which an immune response can be raised. Humanized Abs are exceptionally well-adapted for treatment of diseases and represent attractive candidate antagonists (Jones et al., 1986; Riechmann et al., 1988; Verhoeyen et al., 1988); (U.S. Pat. No. 4,816,567, 1989). Such antibodies may bind to chemokine receptors to inhibit cell migration.

Alternatively, a potential antagonist or agonist may be a closely related protein, for example, a mutated form of a chemokine receptor ligand or other protein that recognizes a chemokine receptor interacting protein, but imparts no effect, thereby competitively inhibiting chemokine receptor action.

Aptamers are short oligonucleotide sequences that can be used to recognize and specifically bind almost any molecule, such molecules may also act antagonistically. The systematic evolution of ligands by exponential enrichment (SELEX) process (Ausubel et al., 1987; Ellington and Szostak, 1990; Tuerk and Gold, 1990) is powerful and can be used to find such aptamers. Aptamers have many diagnostic and clinical uses, including as antagonists. In addition, they are inexpensive to manufacture and can be easily applied in a variety of formats, including administration in pharmaceutical compositions, bioassays, and diagnostic tests (Jayasena, 1999). The RAM assay can also be used as a screen to isolate aptamers de novo.

Quantifying Migratory Cells

Quantifying migratory cells may be accomplished by a large variety of available methods, such as those that assay the amount of DNA, (e.g., the CyQuant Cell Proliferation Kit (Molecular Probes)) and then assaying the generated signal, such as fluorescence. Other methods include counting the cells using a microscope, or labeling cells with a suitable detectable marker, such as dyes (such as Calcein AM (NeuroProbe) or the many labels available from Molecular Probes (Eugene, Oreg.)) or radioactive labeling (e.g. cell surface iodination with $^{135}I$, protein synthesis labeling with $^{35}S$-methionine/$^{35}S$-cysteine or nucleic acid labeling with $^3H$).

Buffers and Cell Culture Media

Buffers that may be used to prepare the various solutions include cell culture media, although serum or other growth and chemotactic factors may be removed so that the results in a cell migration assay are not confounded and can be mostly attributable to the chemokine-chemokine receptor interaction. In some cases, a protein may be added to support the cells, such as various albumins, including bovine serum albumin. Optimal media selection depends on the cell type; that media used to culture the cells usually represents a preferred option. Examples of suitable culture media include Iscove's Modified Dulbecco's Medium (IMDM), Dulbecco's Modified Eagle's Medium (DMEM), Minimal Essential Medium Eagle (MEM), Basal Medium Eagle (BME), Click's Medium, L-15 Medium Leibovitz, McCoy's 5A Medium, Glasgow Minimum Essential Medium (GMEM), NCTC 109 Medium, Williams' Medium E, RPMI-1640, and Medium 199. A medium specifically developed for a particular cell type/line or cell function, e.g. Madin-Darby Bovine Kidney Growth Medium, Madin-Darby Bovine Kidney Maintenance Medium, various hybridoma media, Endothelial Basal Medium, Fibroblast Basal Medium, Keratinocyte Basal Medium, and Melanocyte Basal Medium are also useful. If desired, a protein-reduced or free and/or serum free medium and/or chemically defined, animal component free medium may be used, e.g., CHO, Gene Therapy Medium or QBSF Serum-free Medium (Sigma Chemical Co.; St. Louis, Mo.), DMEM Nutrient Mixture F-12 Ham, MCDB (105, 110, 131, 151, 153, 201 and 302), NCTC 135, Ultra DOMA PF or HL-1 (both from Biowhittaker; Walkersville, Md.), may be used.

If desired, the media may be further supplemented with reagents that limit acidosis of the cultures, such as buffer addition to the medium (such as N,N-bis(2-hydroxyethyl)-2-aminoethanesulfonic acid (BES), bis(2-hydroxyethyl) amino-tris(hydroxymethyl)methane (BIS-Tris), N-(2-hydroxyethyl)piperazine-N'3-propanesulfonic acid (EPPS or HEPPS), glyclclycine, N-2-hydroxyethylpiperazine-N'-2-ethanesulfonic acid (HEPES), 3-(N-morpholino)propane sulfonic acid (MOPS), piperazine-N,N'-bis(2-ethane-sulfonic acid) (PIPES), sodium bicarbonate, 3-(N-tris(hydroxymethyl)-methyl-amino)-2-hydroxy-propanesulfonic acid) TAPSO, (N-tris(hydroxymethyl)methyl-2-aminoethanesulfonic acid (TES), N-tris(hydroxymethyl)methyl-glycine (Tricine), tris(hydroxymethyl)-aminomethane (Tris), etc.). Frequent medium changes and changes in the supplied $CO_2$ (often approximately 5%) concentration may also be used to control acidosis.

Kits

Components to carry out RAM assays may be assembled into kits, containers, packs, or dispensers together with instructions for administration. When supplied as a kit, the different components of the composition may be packaged in separate containers and admixed immediately before use. Such packaging of the components separately may permit long-term storage without losing the active components' functions. For example, a kit may include a cell migration apparatus, a chemokine receptor-bearing cell and a solution comprising an inhibitory migratory concentration of chemokine for the chemokine receptor bearing cell. The solution may be supplied lyophilized.

(a) Containers or Vessels

The reagents included in the kits can be supplied in containers of any sort such that the life of the different components are preserved, and are not adsorbed or altered by the materials of the container. For example, sealed glass ampules may contain lyophilized chemokine or a buffer that has been packaged under a neutral, non-reacting gas, such as nitrogen. Ampules may consist of any suitable material, such as glass, organic polymers, such as polycarbonate, polystyrene, etc., ceramic, metal or any other material typically employed to hold reagents. Other examples of suitable containers include simple bottles that may be fabricated from similar substances as ampules, and envelopes, that may consist of foil-lined interiors, such as aluminum or an alloy. Other containers include test tubes, vials, flasks, bottles, syringes, or the like. Containers may have a sterile access port, such as a bottle having a stopper that can be pierced by a hypodermic injection needle. Other containers may have two compartments that are separated by a readily removable membrane that upon removal permits the components to mix; for example, lyophilized chemokine in one compartment, and a buffer or water in the other. Removable membranes may be glass, plastic, rubber, etc.

(b) Instructional Materials

Kits may also be supplied with instructional materials. Instructions may be printed on paper or other substrate, and/or may be supplied as an electronic-readable medium, such as a floppy disc, CD-ROM, DVD-ROM, Zip disc, videotape, audiotape, etc. Detailed instructions may not be physically associated with the kit; instead, a user may be directed to an internet web site specified by the manufacturer or distributor of the kit, or supplied as electronic mail.

EXAMPLES

The following examples are intended to illustrate and validate the RAM assay concept of the present invention without limitation. The chemoattractant receptor and ligands used to illustrate the invention are chemokine receptors and chemokines. However, any chemoattractant ligand for any chemoattractant receptor may be used. For examples, see Table A.

Examples 1, 2 and 4 demonstrate the effectiveness of the RAM assay, testing specific and non-specific antagonists of CXCR4 as discovered in conventional assays. Example 3 demonstrates the broad applicability of chemoattractant receptors by examining three chemokine receptors.

Example 1

Determining Inhibitory Concentration of SDF (CXCR4)

To obtain a dose response curve for activated lymphocytes expressing cell surface CXCR4, a conventional cell migration assay was used (Bacon et al., 1988; Penfold et al., 1999). Cells were harvested by centrifugation and then resuspended in cell migration buffer (Hank's balanced salt solution (HBSS)/0.1% bovine serum albumin (BSA) at $2.5 \times 10^6$ cells/ml. The CXCR4 ligand stromal-derived factor (SDF-1) was prepared in a concentration series (0.1 nM to 10 mM) by serial dilution in cell migration buffer. At low concentrations, SDF activates cell migration of CXCR4—bearing activated lymphocytes.

SDF ligand was loaded in the bottom chamber of a ChemoTx® cell migration apparatus (5 μm pore polycarbonate polyvinylpyrrolidone-coated filters (Neuroprobe; Gaithersburg, Md.); 29 μl/well) and 20 μl of cell suspension was placed in the upper chamber. The cells were incubated at 37° C. for 150 minutes. The assay was terminated by removing the cells from the upper chamber and membrane surface using a rubber scraper. The cells that migrated to the lower chamber were quantified by the CyQuant assay (Molecular Probes; Eugene, Oreg.), a fluorescent dye method that measures nucleic acid content.

To determine the minimum concentration of SDF to inhibit cell migration, chemokine concentration (X-axis) is plotted against relative fluorescent units (RFUs), correlating to the number of cells migrating (Y-axis) (FIG. 2). Initially as SDF concentration increases, cell migration increases linearly (2, FIG. 2); however, at higher concentrations (3, FIG. 2), migration levels first flatten and then decrease until migration is barely detectable. This bell-shaped curve is typical of chemokine and chemokine receptor-mediated cell migration. In this experiment, 1 µM of SDF was determined to be completely inhibitory; the inhibitory concentration range was 200 nM to 1 µM.

Example 2

Validation of the RAM Assay Using a Viral Polypeptide Antagonist of CXCR4

In the RAM assay, antagonists of chemokine receptors are identified by their ability to activate migration of cells that are incubated with inhibitory chemokine concentrations. To validate the RAM assay, the viral chemokine, vMIP-II, was used as a CXCR4 antagonist. vMIP-II binds with high affinity to CXCR4, blocking receptor signaling and inhibiting cell migration, competing with CXCR4's usual ligand, SDF (Kledal et al., 1997). If CXCR4 expressing cells that are immobilized by inhibitory concentrations of SDF are activated to migrate in the presence of vMIP-II with increased migration, this result would verify the RAM assay principle. For reference and as a control, a conventional cell migration assay was performed. In the conventional assay format, cell migration is inhibited by vMIP-II.

Cell migration was measured using the two formats with the corresponding amounts of SDF chemokine:

(1) a conventional assay (control); 1 nM SDF; and
(2) a RAM assay, 1 µM SDF.

Activated lymphocytes expressing cell surface CXCR4 were harvested as in Example 1. For the conventional assay, a concentration series of vMIP-II was first mixed with activated lymphocytes, and the solution then placed in the upper chamber of a ChemoTx® cell migration apparatus (5 µm pore polycarbonate polyvinylpyrrolidone-coated filters (Neuroprobe), 20 µl/well); 29 µl of a 1 nM solution of SDF was placed in the lower chamber. For the RAM assay, the cells were prepared as for the conventional assay, except the SDF concentration in the lower chamber was 1 µM. The cells were incubated at 37° C. for 150 minutes. The assay was terminated by removing the cells from the upper chamber and membrane surface using a rubber scraper. The cells that migrated to the lower chamber were quantified by the CyQuant assay (Molecular Probes).

Figure 5:
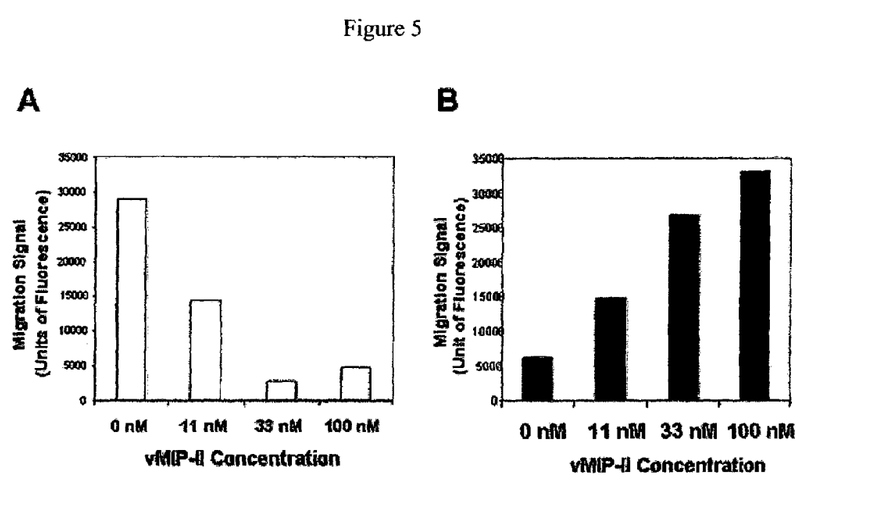
FIG. 5. shows graphs depicting the results from a RAM assay validation experiment using a protein CXCR4 antagonist. Chemokine SDF-mediated cell migration in the presence of the CXCR4 antagonist, vMIP-II, under (A) conventional and (B) RAM conditions.

In the conventional assay (FIG. 5A), cell migration was partially inhibited at 11 nM of vMIP-II; cell migration was further inhibited as the vMIP-II concentration increased (up to 100 nM), verifying that vMIP-II is an antagonist of CXCR4. In the RAM assay format (FIG. 5B), little migration was observed in the absence of vMIP-II. However, migration was activated in the presence of vMIP-II at 11 nM, mirroring the decrease of migration seen in the conventional assay (FIG. 5A). Increased vMIP-11 concentration correlated with an increase in cell migration, with maximal migration being observed at 100 nM.

Example 3

Validation of RAM Assay Using Known Small Molecule Antagonists of CXCR3, CXCR4 and CCR1

RAM assays were performed as described in Example 2, except previously identified small molecule antagonists instead of vMIP-II were used, as well as additional cell types as described in Table 2.

TABLE 2

| | Experimental variables | | |
|---|---|---|---|
| Antagonist[1] | Receptor | Ligand(s) | Cells |
| RAMAG-1 | CXCR3 | I-TAC (250 nM), IP-10 | activated human lymphocytes |
| RAMAG-2 | CXCR4 | SDF-1 | CXCR4-expressing MOLT-4 cells (human T lymphoblast; American Type Tissue Collection (ATCC); Manassas, VA) |
| RAMAG-3 | CCR1 | MIP-1α | THP-1 cells (human monocytic; ATCC) |

[1]As defined using a conventional cell migration assay and further independently confirmed.
[2]Inhibitory concentrations determined as in Example 1.

Figure 6:
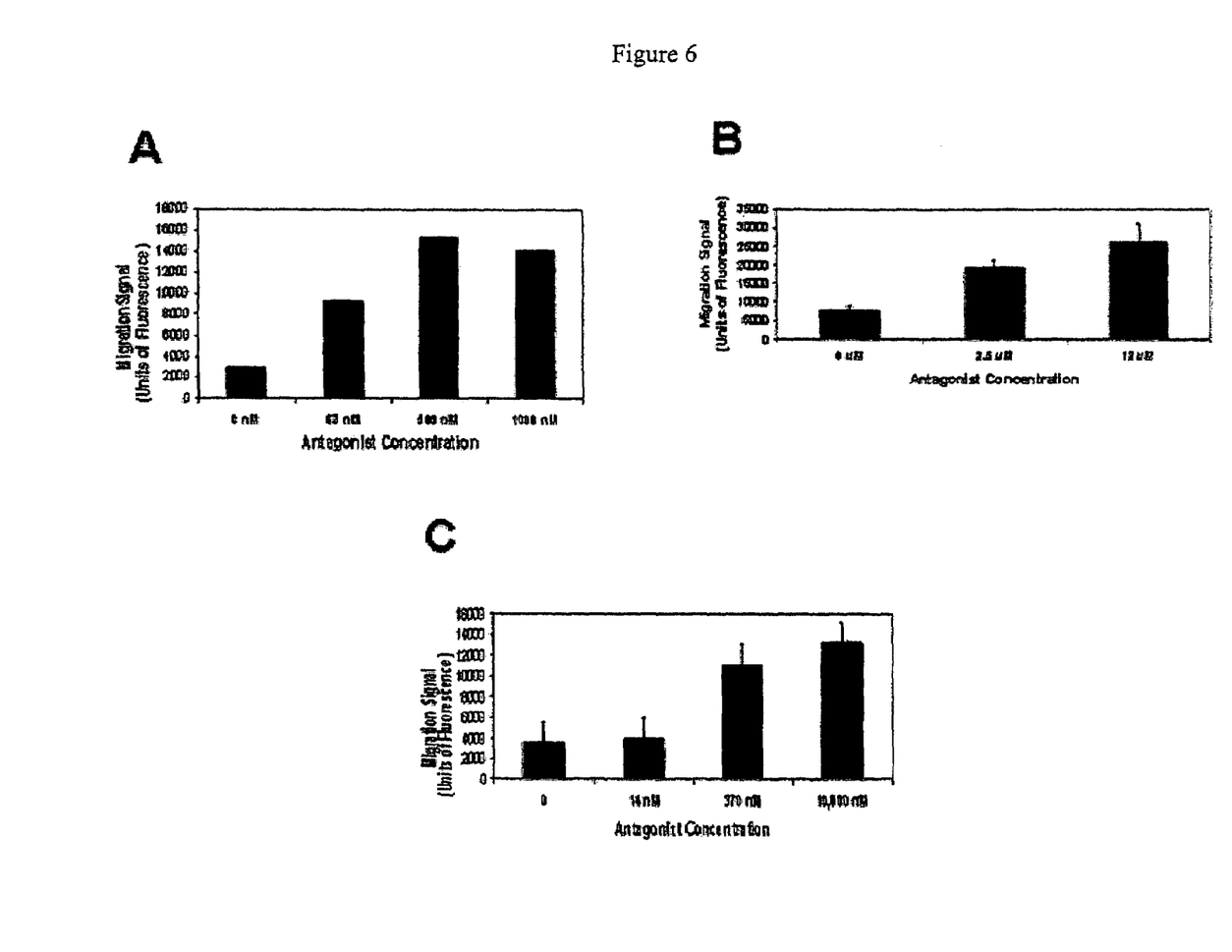
FIG. 6. shows bar graphs depicting the results from a RAM assay validation experiment using small organic CXCR4 antagonists. Chemokine SDF-mediated cell migration in the presence of small organic molecule CXCR4 antagonist (A) RAMAG-1, (B) RAMAG-2 and (C) RAMAG-3.

In the RAM assay, activated lymphocytes incubated in the presence of increasing concentrations of RAMAG-1 and the CXCR3 ligand 1-TAC at 250 nM, cell migration was activated at less than 1 µM (FIG. 6A); as RAMAG-1 concentration increased, migration increased, reaching approaching a maximum at (−6.5 to −5) of RAMAG-1.

At a CXCR4 SDF-1 ligand concentration of 100 nM using CXCR4—expressing MOLT-4 cells, RAMAG-2 activated cell migration at 5 µM (FIG. 5, B). As was observed with RAMAG-1, further activation of migration was seen as the RAMAG-2 concentration increased to 10 µM.

The CCR1 antagonist, RAMAG-3 also gave similar results. In a RAM assay using CCR1-expressing THP-1 cells, RAMAG-3 activated cell migration at 100 nM; as RAMAG-3 concentration increased, so did the migration signal (FIG. 5, C).

Example 4

Validation of RAM Assay Using Known Small Molecules that Non-Specifically Inhibit Cell Migration in CXCR4-Bearing Cells in Conventional Assays This experiment conclusively demonstrates the ability of the RAM assay to discern non-specific and specific chemokine receptor antagonists. A conventional and RAM assays were performed as described in Example 2, but with the following candidate antagonists:

(1) control (no candidate antagonist)
(2) positive control (vMIP-II; a known CXCR4 antagonist)
(3) Known non-specific inhibitors of cell migration:
compound #1
compound #2
compound #3.

Figure 7:
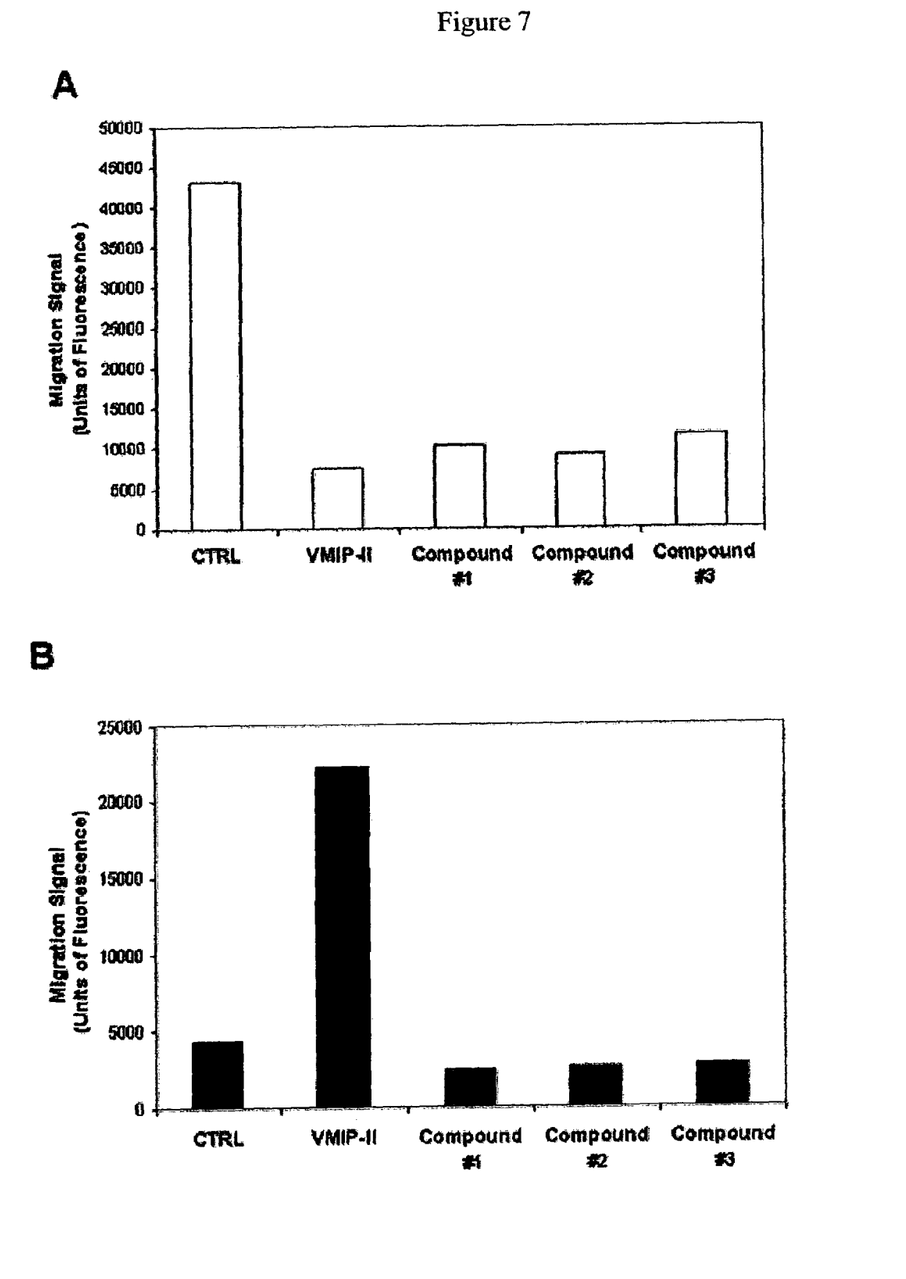
FIG. 7 demonstrates the efficacy of the RAM assay to discern false positive signals. (A) conventional assay, showing inactivation of cell migration by three compounds known to be non-specific; (B) RAM assay, wherein the same three compounds are not indicative of a chemokine receptor antagonist.

As shown in FIG. 7A, control cells migrated, but those incubated with vMIP-II and compounds #1, #2 and #3 showed decreased cell migration. When these same candidate antagonists were subjected to a RAM assay (FIG. 7B), control cells did not migrate, as expected, while vMIP-1'-treated cells did migrate (also expected). However, compounds #1, #2 and #3, known compounds that non-specifically inhibit cell migration in conventional assays, failed to activate cell migration in the RAM assay.

From the results presented in Examples 2-4, the RAM assay distinguishes between non-specific and specific antagonists of chemoattractant receptors, such as chemokine receptors.

REFERENCES

U.S. Pat. No. 4,816,567, 1989. Recombinant immunoglobin preparations.
Ausubel, F. M., R. Brent, R. E. Kingston, D. D. Moore, et al. 1987. Current protocols in molecular biology. John Wiley & Sons, New York.
Bacon, K. B., R. D. Camp, F. M. Cunningham, and P. M. Woollard. 1988. Contrasting in vitro lymphocyte chemotactic activity of the hydroxyl enantiomers of 12-hydroxy-5,8,10,14-eicosatetraenoic acid. *Br J. Pharmacol.* 95:966-74.
Ellington, A. D., and J. W. Szostak. 1990. In vitro selection of RNA molecules that bind specific ligands. *Nature.* 346: 818-22.
Forster, R, A. Schubel, D. Breitfeld, E. Kremmer, et al. 1999. CCR7 coordinates the primary immune response by establishing functional microenvironments in secondary lymphoid organs. *Cell.* 99:23-33.
Jayasena, S. D. 1999. Aptamers: an emerging class of molecules that rival antibodies in diagnostics. *Clin Chem.* 45:1628-50.
Jones, P. T., P. H. Dear, J. Foote, M. S. Neuberger, et al. 1986. Replacing the complementarity-determining regions in a human antibody with those from a mouse. *Nature.* 321: 522-5.
Kledal, T. N., M. M. Rosenkilde, F. Coulin, G. Simmons, et al. 1997. A broad-spectrum chemokine antagonist encoded by Kaposi's, sarcoma-associated herpesvirus. *Science.* 277: 1656-9.
Klein, C., J. I. Paul, K Sauve, M. M. Schmidt, et al. 1998. Identification of surrogate agonists for the human FPRL-1 receptor by autocrine selection in yeast. *Nat. Biotechnol.* 16:1334-7.
Penfold, M. E., D. J. Dairaghi, G. M. Duke, N. Saederup, et al. 1999. Cytomegalovirus encodes a potent alpha chemokine. *Proc Natl Acad Sci US A.* 96:9839-44.
Riechmann, L., M. Clark, H. Waldmann, and G. Winter. 1988. Reshaping human antibodies for therapy. *Nature.* 332:323-7.
Rossi, D., and A. Zlotnik. 2000. The Biology of Chemokines and their Receptors. *Annu. Rev. Immunol.* 18:217-242.
Tuerk, C., and L. Gold. 1990. Systematic evolution of ligands by exponential enrichment: RNA ligands to bacteriophage T4 DNA polymerase. *Science.* 249:505-10.
Verhoeyen, M., C. Milstein, and G. Winter. 1988. Reshaping human antibodies: grafting an antilysozyme activity. *Science.* 239:1534-6.

The invention claimed is:

1. A method, comprising the steps of:
   providing an apparatus comprising an upper chamber and a lower chamber separated by a porous membrane;
   placing cells bearing a chemoattractant receptor in the upper chamber in the presence or in the absence of a candidate antagonist;
   placing an inhibitory concentration of a ligand for the chemoattractant receptor in the lower chamber; and
   measuring migration of cells from the upper chamber to the lower chamber,
   wherein an increased migration of cells to the lower chamber in the presence of the candidate antagonist as compared to the migration of cells in the absence of the candidate antagonist identifies the candidate antagonist as an antagonist to the chemoattractant receptor.

2. The method of claim 1, wherein the candidate antagonist is a small peptide, peptide-like molecule, non-peptidyl organic compound, inorganic compound, nucleic acid or antibody.

3. The method of claim 1, wherein the inhibitory concentration of a ligand for the chemoattractant receptor inhibits chemotaxis greater than or equal to 50% of maximal ligand-activated chemotaxis.

4. The method of claim 1, wherein the inhibitory concentration of a ligand for the chemoattractant receptor inhibits chemotaxis greater than or equal to 95% of maximal ligand-activated chemotaxis.

5. The method of claim 1, wherein the inhibitory concentration of a ligand for the chemoattractant receptor inhibits chemotaxis is 100% of maximal ligand-activated chemotaxis.

6. The method of claim 1, wherein the chemoattractant receptor is selected from the group consisting of C5aR, FPRL-1 receptor, CXCR4, CXCR3, CCR1, and CCR9.

7. The method of claim 6, wherein the ligand for FPRL-1 receptor is selected from the group consisting of w-peptide 1 and w-peptide 2.

8. The method of claim 1, wherein the chemoattractant receptor comprises CB1.

9. The method of claim 1, wherein the chemoattractant receptor is a chemokine receptor and the ligand for the chemoattractant receptor is a chemokine.

10. The method of claim 9, wherein the candidate antagonist is a small peptide, peptide-like molecule, non-peptidyl organic compound, inorganic compound, nucleic acid or antibody.

11. The method of claim 9, wherein the chemokine receptor is CXCR1, CXCR2, CXCR3, CXCR4, CXCR5, CCR1, CCR2, CCR3, CCR4, CCR5, CCR6, CCR7, CCR8, CCR9, CCR10, CCR11, CX3CR1 or XCR1.

12. The method of claim 9, wherein the chemokine is selected from the group consisting of CCR, CXCR, and CX3CR receptor ligands.

13. The method of claim 9, wherein the inhibitory concentration of a ligand for the chemokine receptor inhibits chemotaxis greater than or equal to 50% of maximal ligand-activated chemotaxis.

14. The method of claim 9, wherein the inhibitory concentration of a ligand for the chemokine receptor inhibits chemotaxis greater than or equal to 95% of maximal ligand-activated chemotaxis.

15. The method of claim 9, wherein the inhibitory concentration of a ligand for the chemokine receptor inhibits chemotaxis is 100% of maximal ligand-activated chemotaxis.

16. The method of claim 9, wherein the chemokine receptor comprises CCR5, and the chemokine comprises MIP-1$\alpha$, MIP-1$\beta$, or RANTES.

17. The method of claim 9, wherein the chemokine receptor comprises CXCR4, and the chemokine comprises SDF-1.

18. The method of claim 9, wherein the chemokine receptor comprises CCR9, and the chemokine comprises TECK.

19. The method of claim 9, wherein the chemokine receptor comprises CCR10 and the chemokine comprises CTACK.

20. The method of claim 9, wherein the chemokine receptor comprises CCR6 and the chemokine comprises MIP-3α.

21. The method of claim 9, wherein the chemokine receptor comprises CCR2 and the chemokine comprises MCP-1, MCP-2 or MCP-4.

22. The method of claim 9, wherein the chemokine receptor comprises CXCR3 and the chemokine comprises I-TAC, IP-10, OR MIG.

* * * * *